(12) United States Patent
Mosebach et al.

(10) Patent No.: US 11,759,578 B2
(45) Date of Patent: Sep. 19, 2023

(54) NEEDLE SHROUD ASSEMBLY AND DRUG DELIVERY DEVICE

(71) Applicant: SANOFI, Paris (FR)

(72) Inventors: Carsten Mosebach, Frankfurt am Main (DE); Thomas Mark Kemp, Cambridgeshire (GB)

(73) Assignee: Sanofi, Paris (FR)

(*) Notice: Subject to any disclaimer, the term of this patent is extended or adjusted under 35 U.S.C. 154(b) by 132 days.

(21) Appl. No.: 16/760,592

(22) PCT Filed: Nov. 1, 2018

(86) PCT No.: PCT/EP2018/079914
§ 371 (c)(1),
(2) Date: Apr. 30, 2020

(87) PCT Pub. No.: WO2019/086560
PCT Pub. Date: May 9, 2019

(65) Prior Publication Data
US 2021/0220568 A1  Jul. 22, 2021

(30) Foreign Application Priority Data
Nov. 3, 2017  (EP) .................................... 17306517

(51) Int. Cl.
*A61M 5/32*  (2006.01)
(52) U.S. Cl.
CPC ........ *A61M 5/3245* (2013.01); *A61M 5/3202* (2013.01); *A61M 2005/3268* (2013.01)

(58) Field of Classification Search
CPC .............. A61M 5/3202; A61M 5/3245; A61M 5/3213; A61M 5/2033; A61M 2005/3268; A61M 2005/3254
See application file for complete search history.

(56) References Cited

U.S. PATENT DOCUMENTS

| | | | |
|---|---|---|---|
| 2009/0118676 A1* | 5/2009 | Emmott ................ | A61M 5/002 604/195 |
| 2011/0319864 A1* | 12/2011 | Beller ................. | A61M 5/2033 604/506 |

(Continued)

FOREIGN PATENT DOCUMENTS

| | | |
|---|---|---|
| CN | 103249443 | 8/2013 |
| CN | 104470564 | 3/2015 |

(Continued)

OTHER PUBLICATIONS

PCT International Preliminary Report on Patentability in Application No. PCT/EP2018/079914, dated May 5, 2020, 6 pages.

(Continued)

*Primary Examiner* — James D Ponton
*Assistant Examiner* — Neeraja Gollamudi
(74) *Attorney, Agent, or Firm* — Fish & Richardson P.C.

(57) ABSTRACT

Needle shroud assemblies comprising a needle shroud and a support component. At least one of the needle shroud assemblies includes: a shroud body having an inner surface forming a cavity; a shroud beam arranged on the shroud body and biased radially outwards, wherein the support component is arranged on the inner surface of the shroud body and configured to form an inner radial support surface for the shroud body and/or for the shroud beam.

17 Claims, 4 Drawing Sheets

(56) References Cited

U.S. PATENT DOCUMENTS

| | | | | |
|---|---|---|---|---|
| 2013/0006177 A1* | 1/2013 | Liversidge | ............ | A61M 5/326 |
| | | | | 604/263 |
| 2016/0144132 A1 | 5/2016 | Scanlon | | |
| 2018/0200454 A1* | 7/2018 | Haindl | ................ | A61M 1/1654 |

FOREIGN PATENT DOCUMENTS

| | | | | |
|---|---|---|---|---|
| CN | 105163782 | 12/2015 | | |
| EP | 2578258 | 4/2013 | | |
| EP | 2829296 | 1/2015 | | |
| WO | WO 2012/045831 | 4/2012 | | |
| WO | WO 2014/012996 | 1/2014 | | |
| WO | WO 2014/154498 | 10/2014 | | |
| WO | WO-2014154498 A1 * | 10/2014 | .......... | A61M 5/3204 |
| WO | WO-2016193350 A1 * | 12/2016 | ........ | A61M 5/31578 |
| WO | WO-2016193374 A1 * | 12/2016 | .......... | A61M 5/3204 |

OTHER PUBLICATIONS

PCT International Search Report and Written Opinion in Application No. PCT/EP2018/079914, dated Jan. 28, 2019, 8 pages.

\* cited by examiner

NEEDLE SHROUD ASSEMBLY AND DRUG DELIVERY DEVICE

CROSS REFERENCE TO RELATED APPLICATIONS

The present application is the national stage entry of International Patent Application No. PCT/EP2018/079914, filed on Nov. 1, 2018, and claims priority to Application No. EP 17306517.8, filed on Nov. 3, 2017, the disclosures of which are incorporated herein by reference.

TECHNICAL FIELD

The disclosure generally relates to a needle shroud assembly for a drug delivery device and to a drug delivery device having such a needle shroud assembly.

BACKGROUND

A drug delivery device may completely or partially replace activities involved in parenteral drug delivery from a manual device. Typically, such activities include removal of a protective needle cap, insertion of the needle, providing the force for administering the injection and possibly removal and shielding of the used needle. The shielding of a used needle may be achieved by a needle shroud coupled to a lock mechanism for a needle safety shroud lock before and after the injection.

There remains a need for an improved needle shroud assembly and for an improved drug delivery device comprising such a needle shroud assembly.

SUMMARY

It is an object of the present disclosure to provide an improved needle shroud assembly for a drug delivery device and an improved drug delivery device having such a needle shroud assembly.

The object is achieved by a needle shroud assembly according to claim 1 and by a drug delivery device according to claim 10.

Exemplary embodiments are provided in the dependent claims.

According to the present disclosure, a needle shroud assembly comprises a needle shroud and a support component, the needle shroud comprising a shroud body having an inner surface forming a cavity, a shroud beam arranged on the shroud body and biased radially outwards, wherein the support component is arranged on the inner surface of the shroud body and configured to form an inner radial support surface for the shroud body and/or for the shroud beam.

Such a support component with inner radial support surface supporting the needle shroud, in particular the shroud beam, e.g. shroud lock beam, eliminates the impact of recapping on the function of shroud lock and thus provides needle safety, e.g. continuously. Recapping after use of the drug delivery device may cause a deflection to the shroud beam. If a cap is left in place for a prolonged period, and/or under elevated temperature, the shroud beam can be susceptible to creep. Creep reduces the stress within the shroud beam (lock beam) such that when the cap is removed, the shroud beam does not return to its original form and the overlap with a shroud lock boss within a housing or case is reduced. The added support component generates a radial force on the needle shroud and in particular on the shroud beam so that the shroud beam does not creep.

In an exemplary embodiment, the support component is formed as a sheet metal component. In particular, the support component is a single piece of sheet metal. Furthermore, the support component may be formed from a sheet of steel or aluminium. Alternatively, the support element may be formed as a rigid plastic part or an injection moulding part. A single piece of sheet metal allows a variety of shapes and thin thickness. A single piece of rigid plastic or injection moulding parts may be manufactured easier and more cost-efficiently. In another alternative embodiment, the support element may be a thin metal part which may be used as an inlay during injection molding.

According to a further exemplary embodiment, the support component is multiply bent along a plurality of longitudinal bent edges to form a plurality of support portions. The support component, being bent from a single piece of sheet, is simple to manufacture, resulting in high manufacturing yields and low part cost. Furthermore, the support component is easy to assemble into the needle shroud. The support component allows a radial support surface to avoid creeping of the needle shroud during storage.

In accordance with an aspect of the present disclosure, more than one of the pluralities of support portions comprises a respective tongue axially projecting from the support portion and biased radially outwards. The outwardly bent and axially projecting tongues form further radial support surfaces. In particular, the tongues form a support surface for shroud beams.

Moreover, in an initial state the support component is flat. In a bent state, the support component has a pipe-form or cylinder-form with a polygonal cross section, e.g. a multi-facetted form. This concept increases the strength and stiffness of the support component. The shape of the support component may be varied such that the support component internally encircles the needle shroud to such an extent that a mechanical attachment, e.g. a locking connection between the support component and the needle shroud is created.

In an exemplary embodiment, the support component is bent in such a manner that the support portions are partly overlapped. Hence, in the final bent state, the support component has a nearly circular cross section. During manufacture, nesting is prevented and bulk packaging is allowed. Furthermore, the overlapped carrier or support portions in the final bent state allow compensating manufacturing tolerances of the needle shroud.

Furthermore, the support element comprises an orientation element indicating an assembling orientation.

According to another aspect of the present disclosure, the support element comprises a mounting support or locking element configured to lock a position of the support element relative to the needle shroud. For example, the mounting support or the locking element of the support component comprises holding lugs or holding slots corresponding to retaining slots or retaining lugs of the needle shroud.

In an exemplary embodiment, the needle shroud and the support element are connected in such a manner by the locking element that while the needle shroud moves, the support element moves, too.

According to another aspect of the present disclosure, a drug delivery device comprises a housing having an inner surface forming a cavity to receive a drug container, and a needle shroud assembly as described above, wherein the needle shroud is telescopically retained in the housing.

In an exemplary embodiment, the drug delivery device further comprises a cap removably coupled to the housing.

Moreover, the drug delivery device may comprise a shroud lock mechanism configured to lock a position of the needle shroud relative to the housing of the drug delivery device. In particular, the shroud lock mechanism may comprise the shroud beam, a stop arranged within the housing, a recess arranged proximal of the stop, and the cap, wherein at least a portion of the shroud beam is within the recess when the cap is in place and. The shroud beam abuts the stop after the cap is removed and the needle shroud is locked relative to the housing of the drug delivery device.

According to a further exemplary embodiment, the needle shroud is coupled to a shroud spring for biasing the needle shroud in a distal direction against the housing.

Furthermore, the cartridge or container is prefilled with a drug, in particular an emergency drug, e.g. an allergic drug or a diabetic drug, e.g. hypoglycemia. The drug delivery device is for instance an auto-injector, a pen-injector or a syringe.

In a further embodiment, a piston or stopper slides inside the container to inject the drug. Additionally, the drug delivery device comprises an actuator mechanism for automatically injecting a patient with said drug.

The drug delivery device, as described herein, may be configured to inject a drug or medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector.

The device can include a cartridge-based system that requires piercing a sealed ampule before use. Volumes of medicament delivered with these various devices can range from about 0.4 ml, to 2.25 ml, e.g. 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 5 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 1 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may be activated via an activation mechanism. Such an activation mechanism can include one or more of a button, a lever, a needle shroud, or other activation component. Activation may be a one-step or multi-step process. That is, a user may need to activate one or more activation mechanism in order to cause the automated function. For example, a user may depress a needle shroud against their body in order to cause injection of a medicament. In other devices, a user may be required to depress a button and retract a needle shield in order to cause injection.

In addition, such activation may activate one or more mechanisms. For example, an activation sequence may activate at least two of needle insertion, medicament injection, and needle retraction. Some devices may also require a specific sequence of steps to cause the one or more automated functions to occur. Other devices may operate with sequence independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Further scope of applicability of the present disclosure will become apparent from the detailed description given hereinafter. However, it should be understood that the detailed description and specific examples, while indicating exemplary embodiments of the disclosure, are given by way of illustration only, since various changes and modifications within the spirit and scope of the disclosure will become apparent to those skilled in the art from this detailed description.

BRIEF DESCRIPTION OF THE FIGURES

The present disclosure will become more fully understood from the detailed description given below and the accompanying drawings, which are given by way of illustration only, and do not limit the present disclosure, and wherein.

Corresponding parts are marked with the same reference symbols in all figures.

DETAILED DESCRIPTION

Figure 1A:
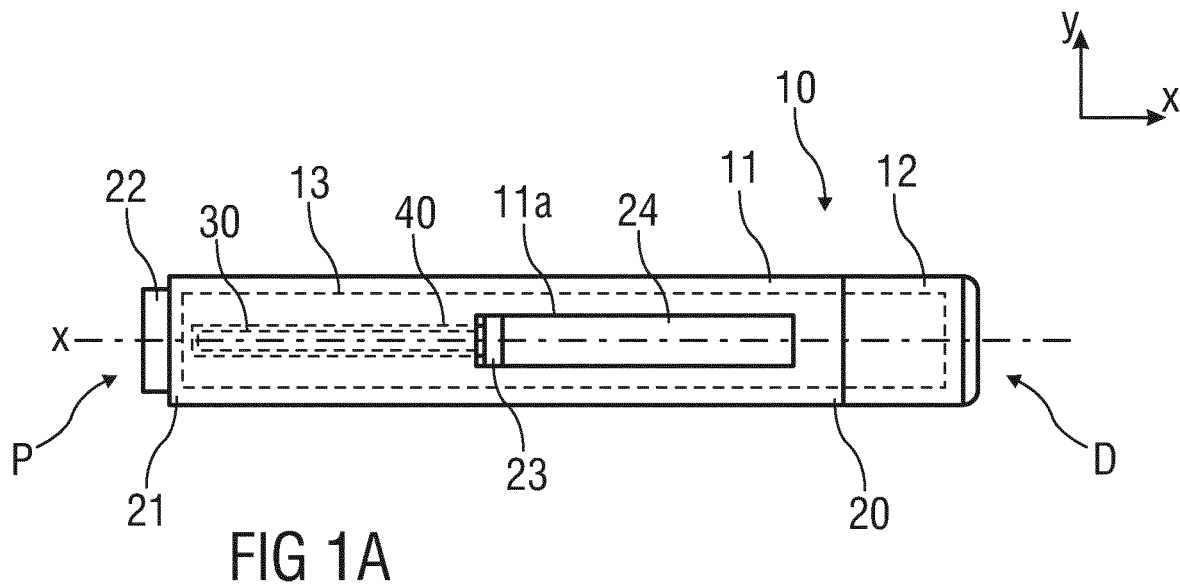
FIGS. 1A to 1B are schematic views of well-known drug delivery devices according to the prior art.
Figure 1B:
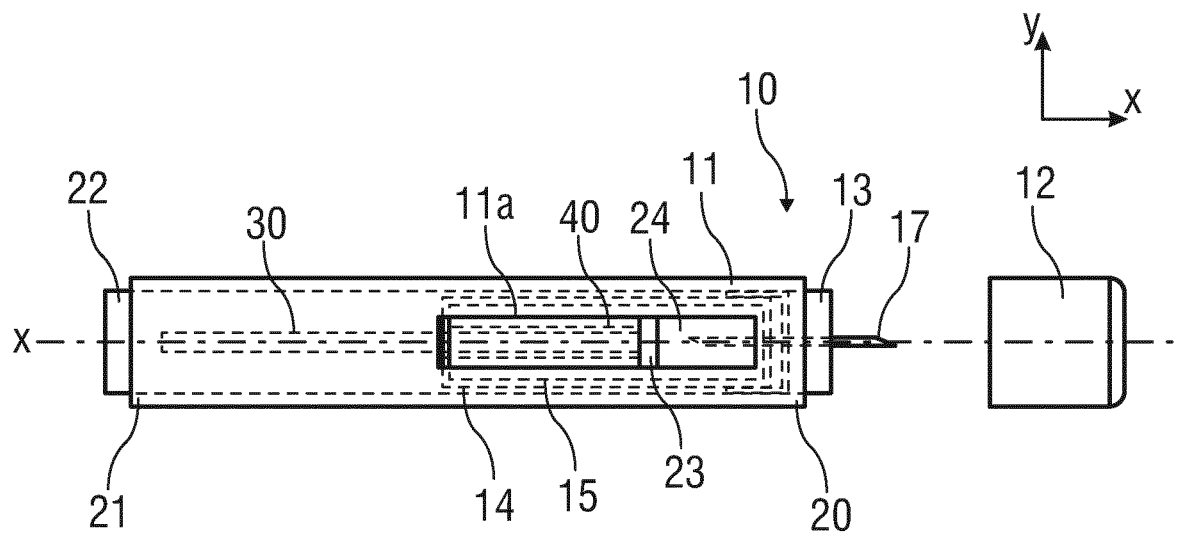

According to some embodiments of the present disclosure, an exemplary drug delivery device 10 is shown in FIGS. 1A and 1B.

Device 10, as described above, is configured to inject a drug or medicament into a patient's body.

Device 10 includes a housing 11 which typically contains a reservoir or cartridge or drug container 24 containing the medicament to be injected (e.g., a syringe or a container) and the components required to facilitate one or more steps of the delivery process.

Device 10 can also include a cap assembly 12 that can be detachably mounted to the housing 11, in particular on a distal or front end D of the device 10. Typically, a user must remove cap assembly or cap 12 from housing 11 before device 10 can be operated.

As shown, housing 11 is substantially cylindrical and has a substantially constant diameter along the longitudinal axis X. The housing 11 has a distal region 20 and a proximal region 21. The term "distal" refers to a location that is relatively closer to a site of injection, and the term "proximal" refers to a location that is relatively further away from the injection site.

Device 10 can also include a needle shroud 13 coupled to the housing 11 to permit movement of the shroud 13 relative to the housing 11. For example, the shroud 13 can move in a longitudinal direction parallel to longitudinal axis X. Specifically, movement of the shroud 13 in a proximal direction can permit a needle 17 to extend from distal region 20 of housing 11. Insertion of the needle 17 can occur via several mechanisms. For example, the needle 17 may be fixedly located relative to housing 11 and initially be located within an extended needle shroud 13. Proximal movement of the shroud 13 by placing a distal end of shroud 13 against a patient's body and moving housing 11 in a distal direction will uncover the distal end of needle 17. Such relative movement allows the distal end of needle 17 to extend into the patient's body. Such insertion is termed "manual" insertion as the needle 17 is manually inserted via the patient's manual movement of the housing 11 relative to the shroud 13.

Another form of insertion is "automated," whereby the needle 17 moves relative to housing 11. Such insertion can be triggered by movement of shroud 13 or by another form of activation, such as, for example, a button 22. As shown in FIGS. 1A & 1B, button 22 is located at a proximal or back end P of the housing 11. However, in other embodiments, button 22 could be located on a side of housing 11. In further embodiments, the button 22 has been deleted and is replaced for instance by a shroud trigger mechanism, e.g. provided by pushing the needle shroud 13 inside the housing when the drug delivery device is put onto an injection side.

Other manual or automated features can include drug injection or needle retraction, or both. Injection is the process by which a bung or piston 23 is moved from a proximal location within a container or cartridge drug container 24 to a more distal location within the cartridge 24 in order to force a medicament from the cartridge 24 through needle 17.

In some embodiments, an energy source, e.g. a drive spring 30 is arranged in a plunger 40 and is under compression before device 10 is activated. A proximal end of the drive spring 30 can be fixed within proximal region 21 of housing 11, and a distal end of the drive spring 30 can be configured to apply a compressive force to a proximal surface of piston 23. Following activation, at least part of the energy stored in the drive spring 30 can be applied to the proximal surface of piston 23. This compressive force can act on piston 23 to move it in a distal direction. Such distal movement acts to compress the liquid medicament within the cartridge 24, forcing it out of needle 17.

Following injection, the needle 17 can be retracted within shroud 13 or housing 11. Retraction can occur when shroud 13 moves distally as a user removes device 10 from a patient's body. This can occur as needle 17 remains fixedly located relative to housing 11. Once a distal end of the shroud 13 has moved past a distal end of the needle 17, and the needle 17 is covered, the shroud 13 can be locked. Such locking can include locking any proximal movement of the shroud 13 relative to the housing 11.

Another form of needle retraction can occur if the needle 17 is moved relative to the housing 11. Such movement can occur if the syringe within the housing 11 is moved in a proximal direction relative to the housing 11. This proximal movement can be achieved by using a retraction spring (not shown), located in the distal region 20. A compressed retraction spring, when activated, can supply sufficient force to the cartridge 24 to move it in a proximal direction. Following sufficient retraction, any relative movement between the needle 17 and the housing 11 can be locked with a locking mechanism. In addition, button 22 or other components of device 10 can be locked as required.

In some embodiments, the housing may comprise a window 11a through which the cartridge 24 can be monitored.

Figure 2:
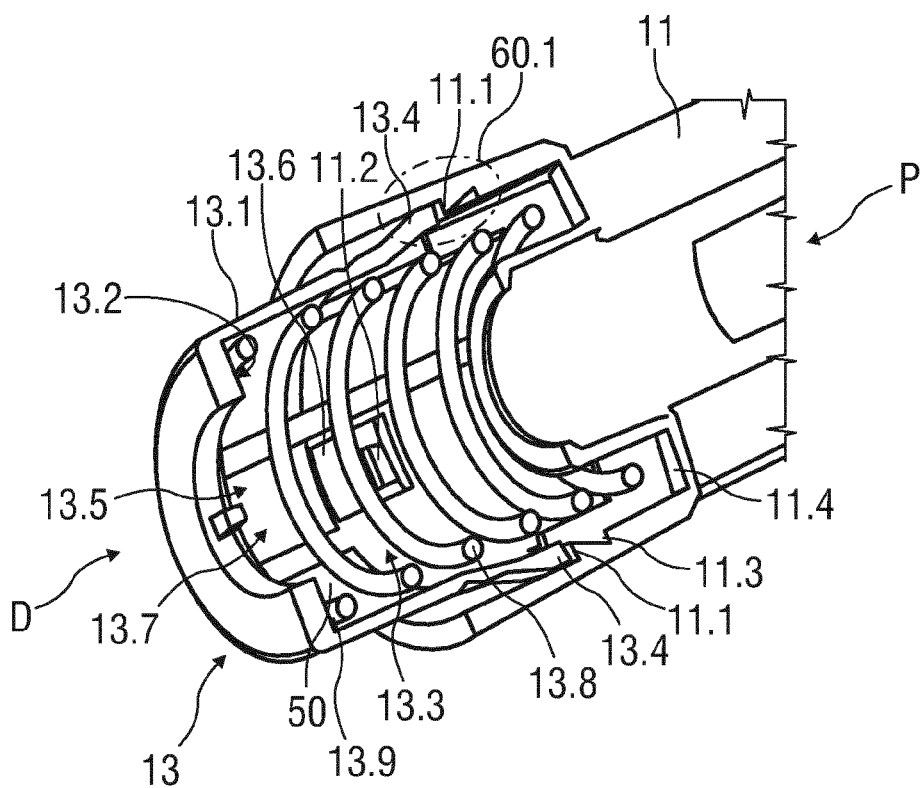
FIG. 2 is a schematic perspective enlarged view of a distal portion of a needle shroud comprising an inner support component.

FIG. 2 shows a perspective enlarged view of a distal portion of the needle shroud 13. The needle shroud 13 is in an extended position and releasably locked in the housing 11 at a distal end of the housing 11, in particular before use.

The needle shroud 13 comprises a shroud body 13.1 having an inner surface 13.2 forming a cavity 13.3.

The needle shroud 13 further comprises a shroud beam 13.4, in particular two or more shroud beams 13.4. The shroud beams 13.4 are arranged on the shroud body 13.1 and biased radially outwards. The shroud beams 13.4 are biased outwards against a rib or stop 11.1 in the housing 11 which form a first shroud lock mechanism 60.1 before use. For example, the shroud beam 13.4 is deformed plastically radially outwards.

In further embodiments, the shroud beams 13.4 are symmetrically distributed around the entire circumference of the needle shroud 13.

The needle shroud 13 serves as a cover for the needle 17 in the extended position, in particular before use or after injection. The needle shroud 13 comprises a distal open end 13.7 through which the needle 17 may extend in a retracted position of the needle shroud 13 (not shown).

FIG. 2 shows the needle shroud 13 in the extended position. In this extended position, the needle shroud 13 extends beyond the needle 17 and is locked in an axial position relative to the housing 11 by the first shroud lock mechanism 60.1. Thus, a risk of needle-stick injury is reduced.

To securely hold the needle shroud 13 in this extended position, the shroud beams 13.4 abut the stop 11.1 after the needle shroud 13 is locked relative to the housing 11.

Furthermore, the needle shroud 13 may comprise an opening 13.6. Optionally, a lug 11.2 of the housing 11 may releasably couple to the opening 13.6 in the extended position of the needle shroud 13.

Moreover, a support component 50 is arranged on the inner surface 13.2 of the shroud body 13.1 and configured to form an inner radial support surface 13.5. The additional support component 50 generates a radial force on the needle shroud 13 and in particular on the shroud beam 13.4 so that the shroud beam 13.4 does not creep due to storage effects and/or high temperatures. The support component 50 is formed in particular as a sheet metal component. Furthermore, the support component 50 may be formed as a one-piece part, in particular as a single piece of sheet metal. For instance, the support component 50 may be formed from a sheet of steel or aluminium. Alternatively, the support element 50 may be formed as a rigid plastic part or an injection moulding part.

Figure 3:
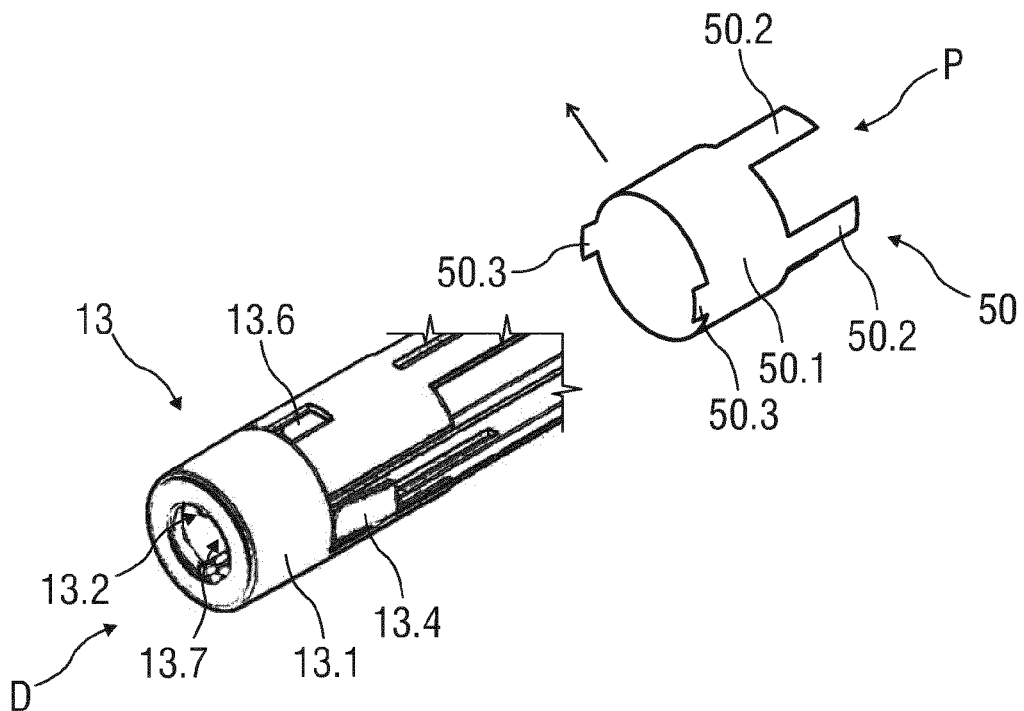
FIG. 3 is an exploded view of a portion of a needle shroud and a support component.

FIG. 3 shows an exploded view of a portion of the needle shroud 13 and the support component 50.

The support component 50 is formed as a sheet metal component. In particular, the support component 50 is a single piece of sheet metal. Furthermore, the support component 50 may be formed from a sheet of steel or aluminium. In other embodiments, the support component 50 may be formed as a rigid plastic part or an injection moulding part, as a single piece moulding part.

The support component 50 may comprise a support portion 50.1. Support tongues 50.2 axially project from the support portion 50.1 in the proximal direction P. In particular, the support tongues 50.2 are biased radially outwards. The outwardly bent and axially projected tongues 50.2 form further radial support surfaces. In particular, the tongues 50.2 form a radial support surfaces for the outwardly bent shroud beams 13.4 when the support component 50 is assembled within the needle shroud 13.

Furthermore, the support component 50 may comprise one or more orientation elements 50.3. The orientation elements 50.3 axially project from the support portion 50.1 in the opposite direction with respect to the support tongues 50.2, in particular in the distal direction D.

In particular, for correct orientation of the support component 50 during assembling within the needle shroud 13, the support component 50 comprises the orientation element 50.3 indicating an assembling orientation. The support component 50 is assembled into the needle shroud 13 as indicated by the extending direction of the orientation element 50.3 away from the support portion 50.1. The orientation element 50.3 is designed as a tactile indicator or visual indicator or a combination of them. In particular, one of the front surfaces of the support component 50 is profiled, e.g. waved or pronged.

Figure 4:
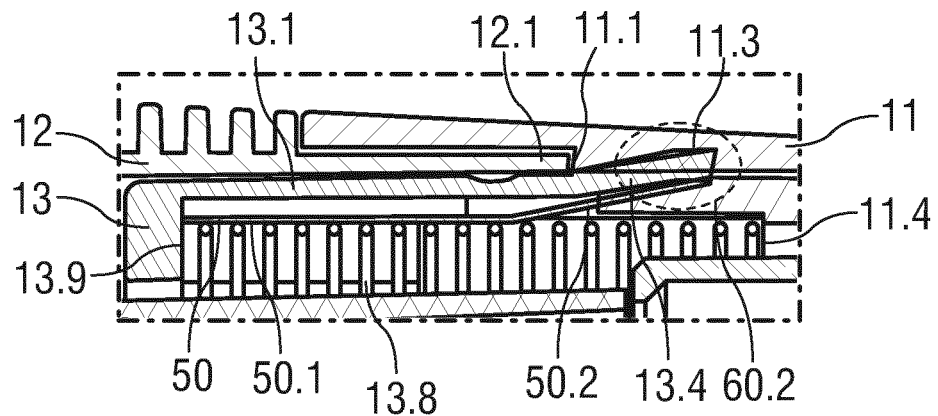
FIG. 4 is a sectional view of a longitudinal section of a shroud lock mechanism.

FIG. 4 shows a sectional view of a longitudinal section of a second shroud lock mechanism 60.2 between the shroud 13 and the housing 11. The drug delivery device 10 is in an assembled and delivery state in which the cap 12 is coupled to the housing 11.

To come into the assembled state, the cap 12 is put on the drug delivery device 10 on its distal end D, in particular on the needle shroud 13. The shape and the form of the shroud beam 13.4 are designed to allow the cap 12 to release the first shroud lock mechanism 60.1 shown in FIG. 2. In particular, the first shroud lock mechanism 60.1 comprises the shroud beam 13.4, and the rib or stop 11.1 arranged within the housing 11 wherein the shroud beam 13.4 and the stop 11.1 interfere with each other such that the shroud beam 13.4 abuts the stop 11.1.

During final assembly, the cap 12 moves inwards and makes sure that the needle shroud 13 also moves inwards causing the shroud beam 13.4 shown in FIG. 2 to deflect so that the shroud beam 13.4 is no longer engaged to stop 11.1. The cap 12 and the needle shroud 13 move inwards until a proximal end 12.1 of the cap 12 abuts the stop 11.1. After disengagement of the shroud beam 13.4 and due to the inward movement of the needle shroud 13, the shroud beam 13.4 engages a recess 11.3 arranged proximal of the stop 11.1 in the housing 11 and forming a second shroud lock mechanism 60.2.

The second shroud lock mechanism 60.2 is configured to lock the retracted position of the needle shroud 13 relative to the housing 11 of the drug delivery device 10 after removing of the cap 2 and before use of the device 10. In particular, the second shroud lock mechanism 60.2 comprises the shroud beam 13.4 and the recess 11.3 arranged proximal of the stop 11.1. Additionally, the needle shroud 13 may be held in position by other components, e.g. by the plunger 40.

At least a portion of the shroud beam 13.4 is arranged within the recess 11.3 when the cap 12 is in place. In this delivery state, the proximal end 12.1 of the cap 12 abuts the stop 11.1 in the housing 11.

The support component 50 is arranged inside the needle shroud 13. The tongue 50.2 is biased outwards and engages the shroud beam 13.4 to hold it in place in the recess 11.3.

For using the device 10 the cap 12 may be removed. The needle shroud 13 is held in the retracted position by the second lock mechanism 60.2 and/or by releasably coupling to another component of the device 10, e.g. to the plunger 40.

After using the device 10, the needle shroud 13 limitedly moves in the distal direction D until the shroud beam 13.4 flexes outwards and abuts the stop 11.1 so that the needle shroud 13 is locked relative to the housing 11 (shown in FIG. 2). In particular, the needle shroud 13 is coupled to a shroud spring 13.8 for biasing the needle shroud 13 in the distal direction D. The ends of the spring 13.8 may directly act on a distal front end 13.9 of the needle shroud 13 and a distal front side of the housing 11.

Figure 5:
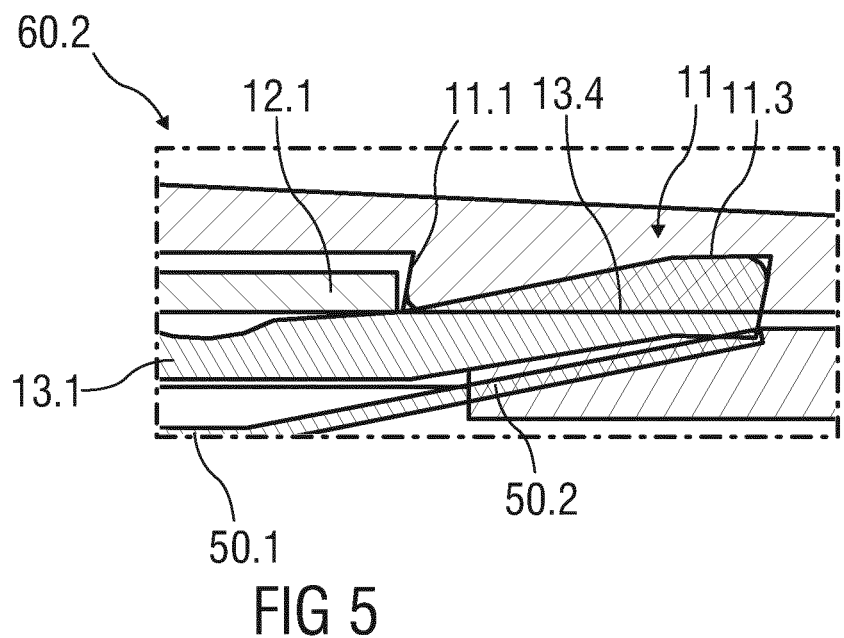
FIG. 5 is an enlarged sectional view of a longitudinal section of a shroud lock mechanism.

FIG. 5 shows an enlarged sectional view of the longitudinal section of the second shroud lock mechanism 60.2 in more detail.

In other embodiments, properties, e.g. form, shape and/or inclination, in particular of the shroud beam 13.4, e.g. of its tip, and/or of the stop 11.1 and/or of the recess 11.3 may vary. For example, the shroud beam 13.4 may have a rib or a part protruding from the tip of the beam 13.4 and/or ribs and/or may be more inclined outwardly to improve initial strain. Further, regarding the first shroud lock mechanism 60.1 the cap 12 may comprise ribs and/or recesses on an internal surface.

Further, the needle shroud 13 may be made from an injection mould material, in particular a glass filled material.

Figure 6:
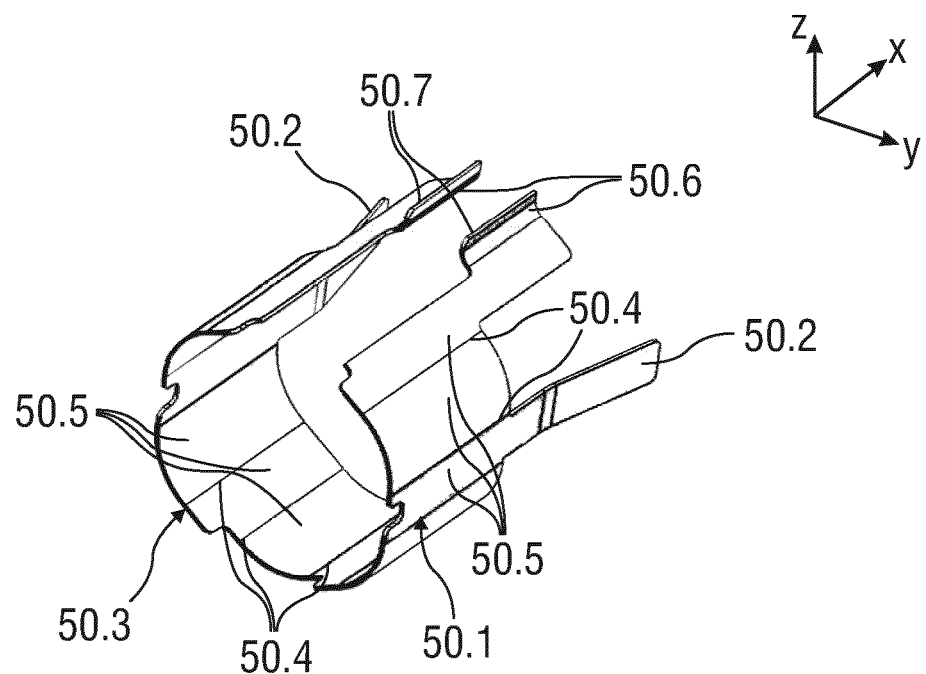
FIG. 6 is a perspective view of an exemplary embodiment of a separate support component.

FIG. 6 shows a perspective view of an exemplary embodiment of a separate support component 50. The support component 50 is formed in particular as a sheet metal component, e.g. a sheet of steel or aluminium.

The support component 50 shown in FIG. 6 is for instance multiply bent along a plurality of longitudinal bent edges 50.4 to form a plurality of support portions 50.5.

In some embodiments, the support component 50, being bent from a single piece of e.g. metal sheet, is flat in an initial state. The metal sheet is bent in such a manner that support portions 50.5 are formed which are separated by the bent edges 50.4.

Moreover, outer portions 50.5 are partly overlapped or are adjoined to each other. These overlapped carrier or support portions 50.5 in the final bent state allow compensating manufacturing tolerances of the needle shroud 13.

In the final bent state, the support component 50 has a nearly circular cross section. In particular, in the final bent state, the support component 50 has a pipe-form or cylinder-form with a polygonal cross section, e.g. a multi-facetted form. This structure increases the strength and stiffness of the support component 50 and, thus, of the needle shroud 13.

In further embodiments, the shape of the support component 50 may be varied such that the support component 50 internally encircles the needle shroud 13 to such an extent that a mechanical attachment, e.g. a locking connection between the support component 50 and the needle shroud 13 is created. The support component 50 allows a radial support surface to avoid shrinking of the needle shroud 13 during storage and to reduce storage stress through increased shroud beam length or reduced thickness and to improve robustness.

In other embodiments, more than one of the pluralities of support portions 50.5 comprises a respective tongue 50.2 axially projecting from the support portion 50.1 and biased radially outwards. The outwardly bent and axially projected tongues 50.2 form further radial support surfaces, in particular support surfaces for shroud beams 13.4 as shown in FIGS. 4 and 5.

According to another embodiment, the support element 50 may comprise a mounting support 50.6. The mounting support 50.6, e.g. a locking element, is configured to lock a position of the support element 50 relative to the needle shroud 13. For example, the mounting support 50.6 of the support component 50 comprises holding lugs or locking elements 50.7 and the needle shroud 13 comprises a retaining slot 13.10 to form a support lock mechanism 70. The locking elements 50.7 are formed for example as flexible or clamping arms which clamp into slot 13.10.

The needle shroud 13 and the support element 50 are connected to each other by the support lock mechanism 70 in such a manner that, while the needle shroud 13 moves the support element 50 moves, too.

Further, the support element 50 comprises orientation element 50.3 indicating an assembling orientation.

Figure 7:
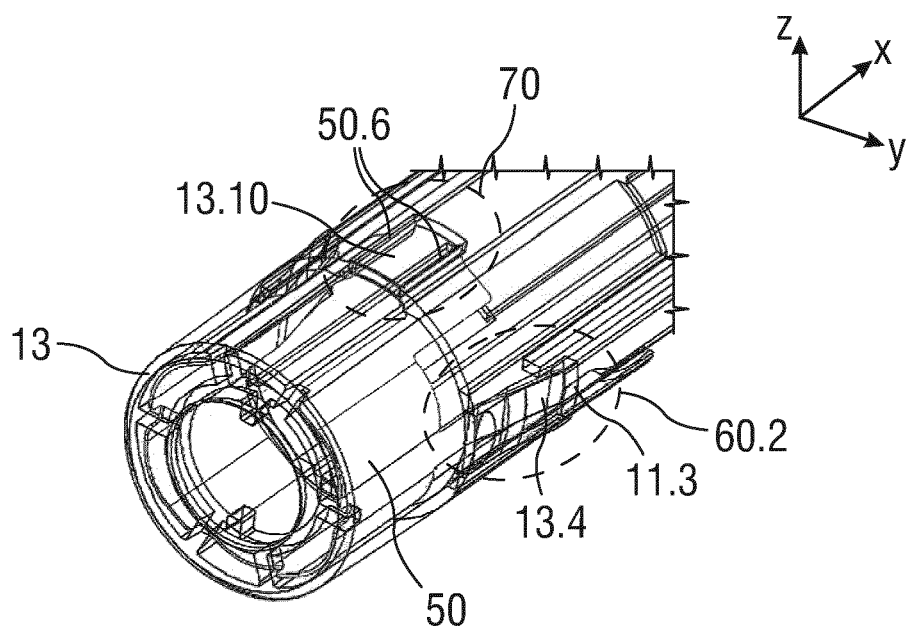
FIG. 7 is an enlarged perspective view of a shroud lock mechanism in an assembled state.

FIG. 7 shows an enlarged perspective view of the second shroud lock mechanism 60.2 and the support lock mechanism 70 in an assembled state.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin; B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin. Exemplary GLP-1, GLP-1 analogues and GLP-1 receptor agonists are, for example: Lixisenatide/AVE0010/ZP10/ Lyxumia, Exenatide/Exendin-4/Byetta/Bydureon/ITCA 650/AC-2993 (a 39 amino acid peptide which is produced by the salivary glands of the Gila monster), Liraglutide/ Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')$_2$ fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present disclosure, which encompass such modifications and any and all equivalents thereof.

LIST OF REFERENCES 10 drug delivery device
11 housing
11.1 stop
11.2 lug
11.3 recess
11a window
12 cap assembly
12.1 proximal end
13 needle shroud
13.1 shroud body
13.2 inner surface
13.3 cavity
13.4 shroud beam
13.5 radial support surface
13.6 opening
13.7 open end
13.8 shroud spring
13.9 distal front end
13.10 retaining slot
17 needle
20 distal region of the drug delivery device 21 proximal region of the drug delivery device
22 button
23 piston
24 cartridge
30 energy source, e.g. drive spring
40 plunger
50 support component
50.1 support portion
50.2 support tongue
50.3 orientation elements
50.4 bent edges
50.5 support portions
50.6 retaining lug
50.7 locking element
60.1, 60.2 shroud lock mechanism
70 support lock mechanism

The invention claimed is:

1. A needle shroud assembly comprising:
a needle shroud; and
a support component;
the needle shroud comprising:
  a shroud body having an inner surface forming a cavity; and
  a shroud beam configured to engage with a housing of a drug delivery device and arranged on the shroud body and biased radially outwards, wherein the support component is arranged on the inner surface of the shroud body and configured to form an inner radial support surface for the shroud body and/or for the shroud beam,
wherein the support component is locked to the needle shroud;
wherein the support component is bent along a plurality of longitudinal bent edges to form a plurality of support portions; and
wherein each of two or more support portions of the plurality of support portions comprises a respective tongue axially projecting from the support portion and biased radially outwards, or
wherein the support component is bent in such a manner that outer support portions of the plurality of support portions are partly overlapped with each other.

2. The needle shroud assembly according to claim 1, wherein the support component is formed as a sheet metal component.

3. The needle shroud assembly according to claim 1, wherein the support component is a single piece of sheet metal.

4. The needle shroud assembly according to claim 1, wherein, in a bent state, the support component has a pipe-form or cylinder-form with a polygonal cross section.

5. The needle shroud assembly according to claim 1, wherein the support component comprises an orientation element indicating an assembling orientation.

6. The needle shroud assembly according to claim 1, wherein the support component comprises a locking element configured to lock a position of the support component relative to the needle shroud.

7. A drug delivery device, comprising:
a housing having an inner surface forming a cavity to receive a drug container; and
a needle shroud assembly comprising:
  a needle shroud; and
  a support component;
  the needle shroud comprising:
    a shroud body having an inner surface forming a cavity; and
    a shroud beam configured to engage with the housing of the drug delivery device and arranged on the shroud body and biased radially outwards, wherein:
the support component is arranged on the inner surface of the shroud body and configured to form an inner radial support surface for the shroud body and/or for the shroud beam, the support component is locked to the needle shroud, and the needle shroud is telescopically retained in the housing.

8. The drug delivery device according to claim 7, further comprising a cap removably coupled to the housing.

9. The drug delivery device according to claim 7, further comprising a shroud lock mechanism configured to lock a position of the needle shroud relative to the housing of the drug delivery device.

10. The drug delivery device according to claim 9, wherein:
the shroud lock mechanism comprises:
  the shroud beam,
  a stop arranged within the housing,
  a recess arranged proximal of the stop, and
  a cap,
at least a portion of the shroud beam is configured to be disposed within the recess when the cap is coupled to the housing and,
the shroud beam is configured to abut the stop after the needle shroud is locked relative to the housing of the drug delivery device.

11. The drug delivery device according to claim 7, wherein the needle shroud is coupled to a shroud spring for biasing the needle shroud in a distal direction against the housing.

12. The drug delivery device according to claim 7, wherein the drug container comprises a drug.

13. The drug delivery device according to claim 7, wherein the support component is a single piece of sheet metal, and/or
wherein the support component is bent along a plurality of longitudinal bent edges to form a plurality of support portions.

14. The drug delivery device according to claim 7, wherein the drug delivery device further comprises a cap removably coupled to the housing, the support component remaining locked to the needle shroud when the cap is removed.

15. The drug delivery device according to claim 7, wherein the support component is permanently locked to the needle shroud.

16. The drug delivery device according to claim 7, wherein the support component is arranged closer to a distal end of the needle shroud than to a proximal end of the needle shroud, wherein the distal end of the needle shroud is arranged to protrude from the housing.

17. A drug delivery device, comprising:
a housing having an inner surface forming a cavity to receive a drug container; and
a needle shroud assembly comprising:
  a needle shroud; and
  a support component;
  the needle shroud comprising:
    a shroud body having an inner surface forming a cavity; and
    a shroud beam configured to engage with the housing of the drug delivery device and arranged on the shroud body and biased radially outwards, wherein the support component is arranged on the inner surface of the shroud body and configured to form an inner radial support surface for the shroud body and/or for the shroud beam, the support component is locked to the needle shroud, such that the support component is configured to move with the needle shroud when the needle shroud moves, the needle shroud is telescopically retained in the housing, wherein the drug delivery device further comprises a cap removably coupled to the housing, the support component remaining in the drug delivery device when the cap is removed.

* * * * *